United States Patent [19]

Weinblatt

[11] Patent Number: 4,623,230
[45] Date of Patent: Nov. 18, 1986

[54] MEDIA SURVEY APPARATUS AND METHOD USING THERMAL IMAGERY

[76] Inventor: Lee S. Weinblatt, 797 Winthrop Ave., Teaneck, N.J. 07666

[21] Appl. No.: 799,190

[22] Filed: Nov. 18, 1985

Related U.S. Application Data

[63] Continuation of Ser. No. 518,614, Jul. 29, 1983, abandoned.

[51] Int. Cl.⁴ .............................................. A61B 3/14
[52] U.S. Cl. .................................................... 351/210
[58] Field of Search ................. 351/209, 210; 250/351

[56] References Cited

U.S. PATENT DOCUMENTS

| | | | |
|---|---|---|---|
| 2,311,914 | 2/1943 | Tiffin et al. | 351/209 |
| 4,034,401 | 7/1977 | Mann | 351/210 X |
| 4,146,311 | 3/1979 | Murr | 351/210 X |

OTHER PUBLICATIONS

Arzbaecher, On-Line Monitoring and Digital Processing of Human Eye-Fixations, 23rd Annual Conf of Enginnering in Medicine & Biology, Wash. DC, Nov. 1970.

Primary Examiner—Rodney B. Bovernick
Attorney, Agent, or Firm—Natter & Natter

[57] ABSTRACT

A survey method and apparatus for monitoring visual observation of a transitionally viewed display. The procedure includes transmitting infrared radiation from behind the display and directed at the path of travel of a moving observer. A radiation detector receives reflected radiation and generates a thermal image corresponding to radiance variations. Retinal eye reflection from the observer is readily distinguishable in the thermal image and provides a positive indication that the observer's line of sight is vectored upon the display.

5 Claims, 3 Drawing Figures

MEDIA SURVEY APPARATUS AND METHOD USING THERMAL IMAGERY

This is a continuation of application Ser. No. 518,614 filed 07/29/83 now abandoned.

TECHNICAL FIELD

This invention relates to media survey techniques and especially to a data acquisition system using radiant energy.

In particular the appartus of this invention concerns a thermal imaging device and method for monitoring viewer response to visual stimuli.

BACKGROUND ART

The effectiveness of media promotions and corresponding advertising rates were strongly influenced by the size and scope of the potential audience which could be reached by that format.

With regard to outdoor billboard advertising, it had been extremely difficult within the industry to sample or otherwise predict prospective viewer response since there was no way of quantitatively measuring when an advertising display was observed and the frequency of such observations. A further difficulty in accumulating such data resulted because those outdoor displays were placed along highways having fast-moving vehicular traffic.

Prior attempts to collect and record information regarding audience exposure to billboard advertising employed such devices as a pressure sensitive tape placed across the roadway which functioned as a counter and thus indicated traffic flow or density. That system, however, merely provided numerical data relative to the number of vehicles but failed to take into consideration whether the occupants within the vehicles observed the roadside display.

Another monitoring arrangement utilized concealed cameras that were mounted behind or in close proximity to the billboard and were aimed at the passing automobiles. A distinct shortcoming of that system was that it was based upon the recording and counting of those occupants within the vehicles that were facing in the direction of the billboard. That concept relied upon head movement toward the display as an indication of viewer observation of the display. It should be apparent that that survey method failed to appreciate that a subject viewer did not necessarily need to turn one's head in order to view the roadside display especially if the billboard was visible at some distance along the highway and conversely head movement in the direction of the billboard was not an absolute indicator that the individual was looking at the billboard. Furthermore, tinted automobile windows and the usual accumulation of dirt severely interfered with the ability to observe the occupants. This was also compounded during nighttime when visibility within the automobile was drastically limited and during hazy weather conditions.

Another disadvantage of the previous survey methods was that they could not provide accurate data regarding spectator perception because there was no way of determining when the viewer's line of sight was directed at the advertisement.

Although the utilization of radiant energy for monitoring eye movement was shown in U.S. Pat. Nos. 3,379,885 and 3,450,446, those devices were not directed to media survey methods using thermal imagery as in the present invention. Additional U.S. patents which disclosed apparatus relying upon eye reflected light include U.S. Pat. Nos. 4,034,401, 3,986,030 and 3,712,716. It should be noted that those last mentioned devices were not concerned with sensing eye movement from a subject in relative motion.

DISCLOSURE OF THE INVENTION

Briefly, the nature of this invention involves an apparatus and method using thermal imaging for acquiring data regarding viewer response to a transitionally viewed display. The invention is further directed to a method for discerning when a moving subject's field of view is vectored upon a stationary billboard.

The concept of this invention relies upon a radiant energy scan for illuminating a moving subject when within the scan field without detection by the subject and for optically receiving, focussing and amplifying reflected radiation from the subject so as to provide a visible image. The invention further utilizes the selective absorption characteristics of infrared radiation for enhancing areas of the infrared image. In this regard, it has been found that the light sensitive ocular membrane of the posterior portion of the eye responds to infrared stimulation by becoming highly reflective. A radiation sensing device in registration with this ocular radiance, effectively highlights the viewer's eyes within the thermal image and tracks the sight line.

In view of the foregoing, it should be apparent that the present invention overcomes many of the shortcomings of the prior art and provides an improved media survey apparatus and method using thermal imagery.

Having thus summarized the invention, it will be seen that it is an object thereof to provide a survey apparatus and method of the general character described herein which is not subject to the aforementioned disadvantages.

Another object of this invention is to provide a survey apparatus and method using thermal imagery which is adaptable for monitoring observation of a transitionally viewed display.

Specifically, it is an object of this invention to provide a survey apparatus and method using thermal imaging for indexing eye movement of passengers within moving vehicles.

With these ends in view, the invention finds embodiment in certain combinations of elements and arrangements of parts by which the objects aforementioned and certain other objects are hereinafter attained, all as more fully described with reference to the accompanying drawings and the scope of which is more particularly pointed out and indicated in the appended claims.

BRIEF DESCRIPTION OF THE DRAWINGS

In the accompanying drawings in which is shown a possible exemplary embodiment of the invention.

BEST MODE FOR CARRYING OUT THE INVENTION

Figure 1:
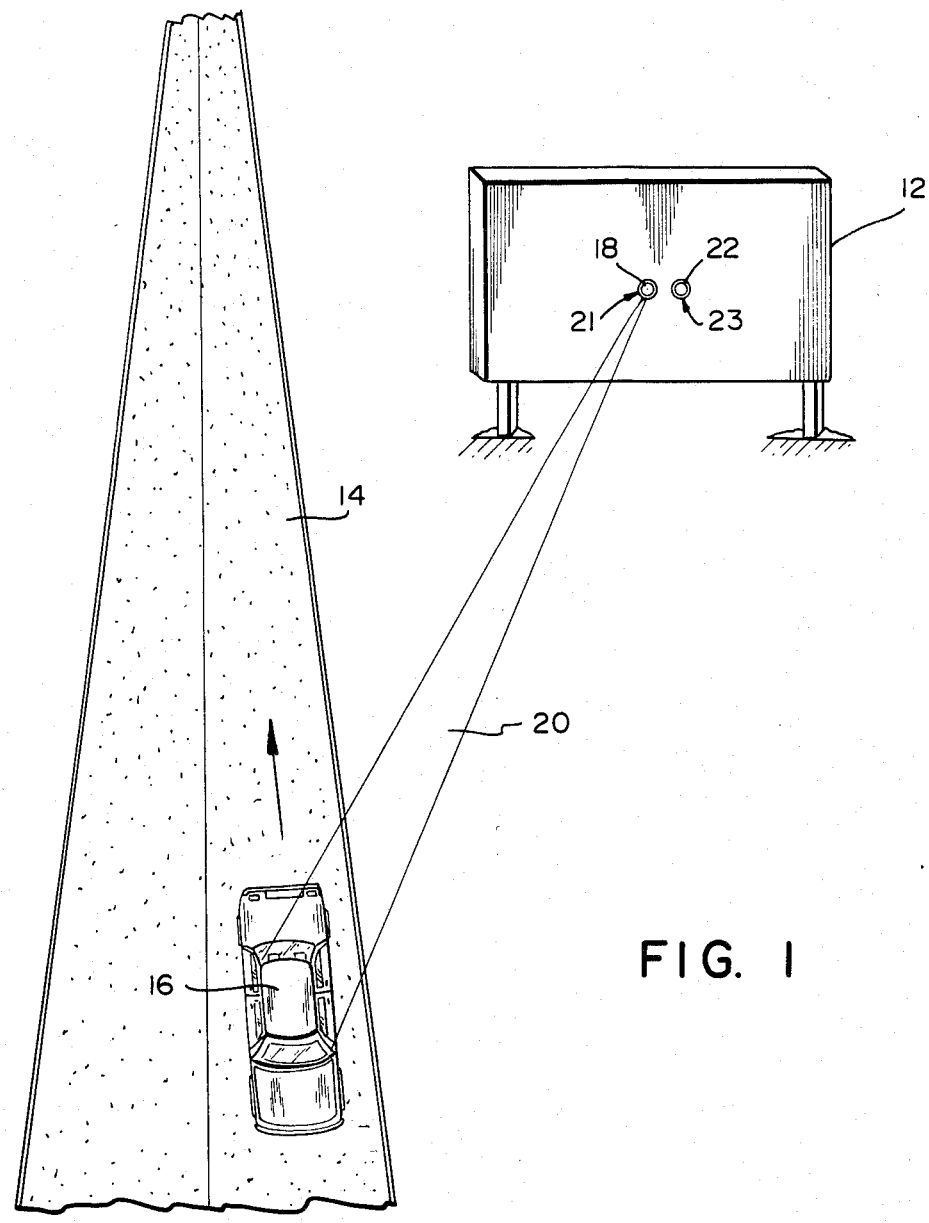
FIG. 1 is a pictorial representation illustrating a highway with a moving vehicle and a billboard having an infrared scan being emitted from a source therein.

Referring now in detail to the drawings, there is shown a survey apparatus and method of this invention being denoted generally by the reference numeral 10. For the purpose of this exemplary embodiment, FIG. 1 illustrates the application of this invention as used for acquiring a data base as to the readership of a billboard 12. The billboard 12 is typically mounted alongside a highway 14 approximately 10 feet (3 meters) therefrom and is about 25 feet (7.5 meters) in height with the width approximately 25 to 75 feet (7.5 to 22.5 meters). Visual stimuli in a form of an advertisement, pictorial representation, written or other material is customarily displayed on the billboard 12 in such manner that it faces in the direction of oncoming vehicular traffic. For the purpose of this illustration, an automobile 16 is shown with an arrow indicating the direction of travel.

In accordance with this invention, a source of radiation is continuously emitted as from an infrared transmitter 18 mounted within or behind the billboard 12 and projects a fixed output scan or beam 20 through an aperture 21 in the billboard 12. The radiation beam 20 is directed approximately 100 feet (30 meters) down the highway 14 for traversing the moving vehicle 16. It should also be noted that the radiation beam 20 is within the invisible light spectrum and cannot be detected by the vehicle occupants nor should they experience any distraction or discomfort.

The infrared radiation will be selectively absorbed and reflected from the occupants within the vehicle 16 and surrounding surfaces. The apparatus of this invention is intended to receive the reflected radiation particularly from the face of the occupant. Futhermore, since infrared radiation is not scattered by atmospheric haze, objects ordinarily invisible because of intervening haze will be detectable. For this purpose, a telephoto lens 22 centrally located and mounted behind the billboard 12 is aimed through an opening 23 in the same direction as the transmitter 18. The reflected radiation from the occupant's face, designated by the reference numeral 25, will be received by the telephoto lens 22. These rays 25 are transmitted to a light image amplifier 24 and then to a detector device such as an infrared sensitive television camera 26. The lens focal length of the camera 26 should be adjusted for infrared however, this is not critical and the infrared will be detected even if slightly out of focus. A radiance variation, as produced by the reflected radiation 25, can be sensed by the camera 26 or an equivalent detector which can generate signals corresponding to the intensity of infrared radiation and provide a display input to produce a visible image. In accordance with current technology, the visible image can be displayed synchronously with and corresponding to the spacial distribution of the infrared radiation. In this connection, the infrared image can be displayed on a cathode ray tube, on flat panel displays using liquid crystal elements, light emitting diodes or otherwise can be stored using known analog or digital data processing methods. In the typical embodiment shown, the generated signals from camera 26 are fed to a video tape recorder 28 for storage and later use for survey analysis.

An important aspect of this invention, however, is the interpretation of the thermal visual image and the discernment as when the subject occupant's line of sight is directed toward the billboard 12 for providing positive indication that the subject's eyes are viewing the display.

Figure 2:
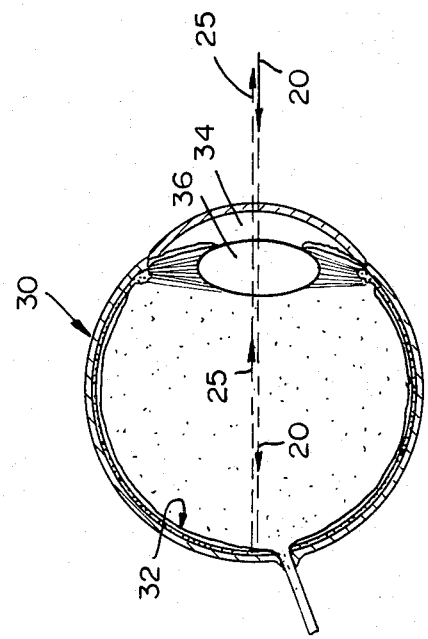
FIG. 2 is a schematic view illustrating the infrared emitting source, a high-powered telephoto lens mounted in the billboard, an infrared sensitive TV camera, and a video tape recorder.
Figure 3:
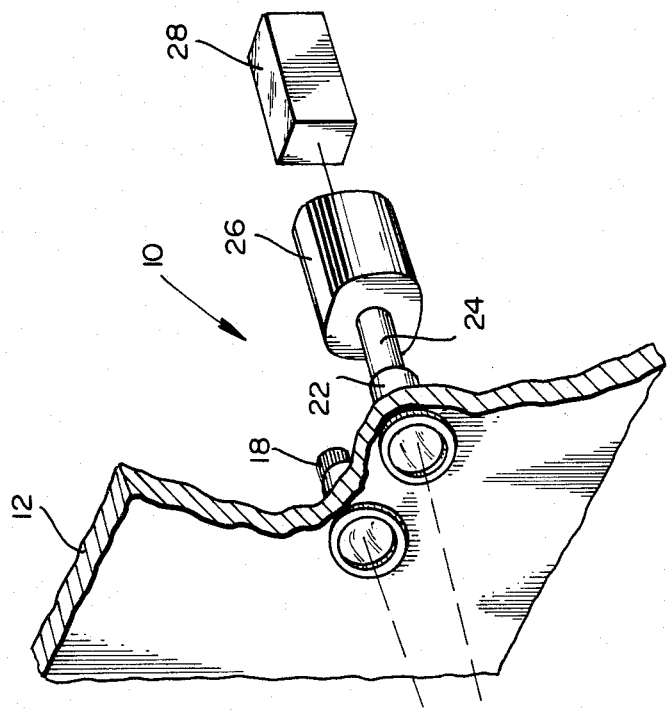
FIG. 3 is an enlarged diagramatic view of an eyeball showing the infrared radiation as reflected from the retina and passing through the pupil.
Figure 3:
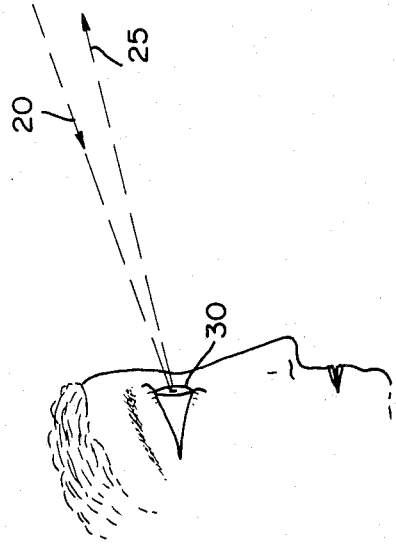

With regard to biological effects of infrared radiation upon human tissue, reference is made to FIGS. 2 and 3 wherein there is shown an eye structure 30 including a pupil 34 and a lens 36. It has been found that the light sensitive membrane forming the retina 32 within the posterior portion of the eye 30 reflects a larger quanta of infrared radiation through the lens 36 and the pupil 34 than that of the surrounding facial tissue. When the subject occupant's line of sight is directed to the billboard 12, the retinal reflected radiation 25 will be coincident with the sight path and will be detectable by the camera 26 as shown in FIG. 2. Since the retinal reflected radiation 25 is more intense than surrounding radiance, the subject's eyes will appear more brilliantly on the visual thermal image. This will thus provide an indication that the subject occupant is looking at the billboard display. It should thus be apparent that the recorded imagery on the video tape recorder 28 can be interpreted for retinal coincidence to determine when the occupant's field of sight is directed toward the billboard 12 and this information can thus be utilized for compiling a data base.

Thus it will be seen that there is provided a media survey apparatus and method using thermal imagery for monitoring viewer response to visual stimuli which is well adapted to meet the conditions of practical use.

Since various possible embodiments might be made of the present invention and various changes might be made in the exemplary embodiment set forth, it is to be understood that all materials set forth or shown in the accompanying drawings is to be interpreted as illustrative and not in a limiting sense.

Having thus described the invention, there is claimed as new and desired to be secured by Letters Patent:

1. A media survey method for monitoring visual observation by a subject viewer of a transitionally viewed display comprising the steps of:
    (a) directing a beam of infrared radiation from a display toward the subject without any intervening reflection of the beam,
    (b) detecting reflected radiation from the subject including retinal eye reflected radiation along the line of sight when the display is viewed by the subject,
    (c) generating representative signals corresponding to the intensity of the reflected radiation,
    (d) processing the signals to provide a thermal image, and
    (e) discriminating retinal eye reflected radiation on the thermal image to provide a positive indication of the visual observation by the subject of the display.

2. A method for monitoring visual observation of a transitionally viewed display as claimed in claim 1 wherein an infrared radiation source is transmitted from a location either within or behind the display.

3. A method for monitoring visual observation of a transitionally viewed display as claimed in claim 2 wherein the reflected radiation is detected by sensing means located either within or behind the display.

4. A survey method for monitoring visual observation of a transitionally viewed display as claimed in claim 1 further including the step of
    (f) recording the processed signals.

5. A method for monitoring visual observation of a transitionally viewed display as claimed in claim 1 wherein the subject is in motion relative to the display.

* * * * *